United States Patent [19]
Chapuis et al.

[11] Patent Number: 6,020,527
[45] Date of Patent: Feb. 1, 2000

[54] STEREOSPECIFIC ISOMERISATION OF ALLYL AMINES USING CHIRAL PHOSPHOROUS LIGANDS

[75] Inventors: Christian Chapuis, Mies; Michel Barthe, Chancy, both of Switzerland

[73] Assignee: Firmenich SA, Geneva, Switzerland

[21] Appl. No.: 09/282,418

[22] Filed: Mar. 31, 1999

[30] Foreign Application Priority Data

Apr. 7, 1998 [CH] Switzerland ............................ 0822/98

[51] Int. Cl.$^7$ .................................................. C07C 249/00
[52] U.S. Cl. .......................... 564/248; 564/278; 564/279; 564/271; 564/305; 564/355; 564/383; 564/444; 564/503; 564/509
[58] Field of Search ..................................... 564/383, 355, 564/248, 278, 279, 271, 305, 444, 503, 509

[56] References Cited

U.S. PATENT DOCUMENTS

| | | | |
|---|---|---|---|
| 4,695,631 | 9/1987 | Otsuka et al. | 544/170 |
| 5,488,172 | 1/1996 | Cereghetti et al. | 568/13 |
| 5,510,503 | 4/1996 | Laue et al. | 556/21 |
| 5,627,293 | 5/1997 | Pugin | 556/11 |
| 5,783,715 | 7/1998 | Okuda et al. | 106/31.26 |

FOREIGN PATENT DOCUMENTS

| | | |
|---|---|---|
| 0 068 506 | 11/1984 | European Pat. Off. . |
| 0 135 392 | 2/1988 | European Pat. Off. . |
| 0 156 607 | 11/1988 | European Pat. Off. . |
| 0 643 065 | 3/1995 | European Pat. Off. . |
| 0 398 132 | 9/1995 | European Pat. Off. . |
| 0 729 969 | 9/1996 | European Pat. Off. . |
| 0 849 274 | 6/1998 | European Pat. Off. . |
| 62-178594 | 1/1986 | Japan . |
| WO 98/01457 | 1/1998 | WIPO . |

*Primary Examiner*—Samuel Barts
*Attorney, Agent, or Firm*—Pennie & Edmonds LLP

[57] ABSTRACT

The present invention describes a stereospecific process for the isomerization of prochiral allyl amines into chiral enamines and imines, using Rh, Ir or Ru catalysts which carry chiral phosphine ligands derived from ferrocenes, which may be immobilized on a solid carrier, or from steroides. The process is in particular appropriate for the production of chiral citronellal, which can be obtained in optical purities of greater than 95%.

14 Claims, No Drawings

STEREOSPECIFIC ISOMERISATION OF ALLYL AMINES USING CHIRAL PHOSPHOROUS LIGANDS

BRIEF SUMMARY OF THE INVENTION

The present invention relates to the field of organic synthesis. More particularly, it relates to a stereospecific process for the isomerisation of allyl amines as defined by the formula (I) below, wherein there are used complexes of certain transition metals with phosphine compounds which are either planar-chiral ferrocenes known under the name of JOSIPHOS® and derivatives thereof, or diphosphine ligands derived from steroids.

BACKGROUND OF THE INVENTION

The isomerisation of allyl amines which may be prochiral using complexes of rhodium, iridium or ruthenium such as, for example, those represented by the formulae [Rh(P—P)*diene]$^+$X$^-$, [Rh(P—P)*$_2$]$^+$X$^-$, [Ru(CH$_3$COO)$_2$(P—P)*] or [RuY$_2$(P—P)*], in which (P—P)* is a bidentate phosphine ligand, "diene" stands for a diolefine such as cyclooctadiene or norbornadiene, X$^-$ is an anion such as a halide, BF$^-_4$, PF$^-_6$ or ClO$^-_4$, and Y is a halide, is known since several years. The isomerisation reaction gives the corresponding enamines or imines which are thereafter hydrolyzed to obtain chiral aldehydes, such as, for example, citronellal, methoxycitronellal or hydroxycitronellal. These latter are highly appreciated compounds in perfumery.

The above-mentioned processes are the object of several publications of which there are cited here the patents EP-B-068 506, 135 392 and 156 607 (patentee: Takasago Perfumery Co.) and JP 61-19203 of the same patentee, as well as the patent EP-B-398 132 (patentee: Hoffmann-La Roche AG) and the patent application EP 643 065 (applicant: Bayer AG). All the processes described in these references make use of catalysts which carry chiral bidentate phosphines which are derived from biphenyl or binapthyl system. The best known ligand for this isomerisation reaction (and which, moreover, also finds use in other catalytical application is the ligand known under the name of BINAP, which is represented by the following formula (IV)

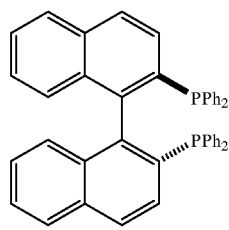

(IV)

Ph = phenyl

We were not able to find in any prior art reference on the isomerisation of allylamines, in particular the stereospecific isomerisation, any example for the use of another ligand type as the one described above, namely a bidentate phosphine ligand derived from atropisomeric biaryles.

It may thus be surprising that we have succeeded to develop another catalytic system which uses chiral phosphorous ligands of a different type, derived from ferrocene, the chirality of which is not based on an atropic isomerism. In a further embodiment of the invention, there are used phosphine ligands which are derived from steroids. All these ligands have shown to be very useful for the above-mentioned isomerisation of prochiral allylamines.

DETAILED DESCRIPTION OF THE INVENTION

Therefore, the object of the present invention is a process for the stereospecific isomerisation of prochiral allylic systems represented by the formula

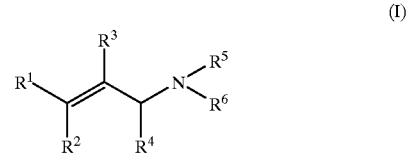

(I)

in which R$^1$≠R$^2$, each being selected from the group consisting of alkyl and alkenyl groups containing from 1 to 12 carbon atoms, aryl groups, optionally substituted by a hydroxy group, R$^3$ and R$^4$ are, independently from each other, selected from the group consisting of hydrogen, alkyl and alkenyl groups from C$_1$ to C$_{12}$ and aryl groups, R$^5$ is selected from the group consisting of hydrogen and alkyl and cycloalkyl groups containing from 1 to 8 carbon atoms, R$^6$ is selected from the group consisting of alkyl and cycloalkyl groups containing from 1 to 8 carbon atoms, or R$^5$ and R$^6$ are taken together with the nitrogen atom to form a ring selected from the group consisting of 5-membered rings, 6-membered rings and 6-membered rings which further contain an oxygen atom, into the group of compounds consisting of enamines as represented by the formula

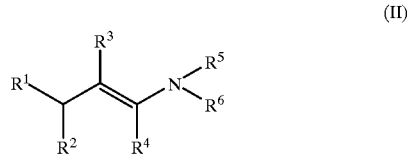

(II)

in which the symbols R$^1$–R$^6$ are as defined above, and imines as represented by the formula

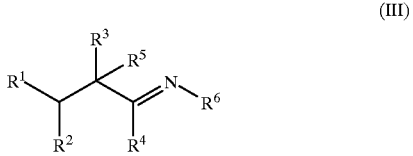

(III)

in which the symbols R$^1$–R$^4$ and R$^6$ are as defined above and R$^5$ is hydrogen, by means of catalysts selected from the group consisting of Rh, Ir and Ru compounds carrying at least one chiral phosphorous ligand, wherein said ligand is a compound represented by the formula (V)

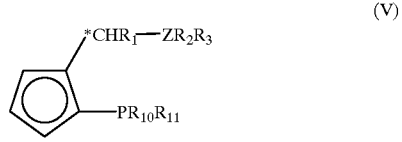

(V)

-continued

Fe
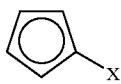
X in which the carbon atom marked by an asterisk is an asymmetric carbon atom, X is hydrogen or a bridging group bonded to a polymer and represented by formula $(A)_n$—B—P in which n is 0 or 1, A is an appropriate spacer group containing at least one atom of oxygen, sulfur, silicon, nitrogen or carbon, B is a linking group between the cyclopentadienyl rest and the polymer P when n=0, or between A and P when n=1, and P is an organic or inorganic polymer, A. Z stands for a phosphorous atom; $R_1$ is selected from the group consisting of alkyl groups from $C_1$ to $C_8$, phenyl groups, optionally substituted by 1 to 3 alkyl or alkoxy groups from $C_1$ to $C_4$; $R_2$, $R_3$, $R_{10}$ and $R_{11}$ are, independently from each other, selected from the group consisting of alkyl groups from $C_1$ to $C_2$, cycloalkyl groups from $C_5$ to $C_{12}$, optionally substituted by an alkyl or alkoxy group from $C_1$ to $C_4$, and phenyl groups optionally carrying from 1 to 3 substituents selected from the group consisting of alkyl and alkoxy groups from $C_1$ to $C_4$, —$SiR_4R_5R_6$, halides, —$SO_3M$, —$CO_2M$, —$PO_3M$, —$NR_7R_8$ and —$[^+NR_7R_8R_9]Y^-$; or $R_2$, $R_3$, $R_{10}$ and $R_{11}$ represent, independently from each other, a group of formula

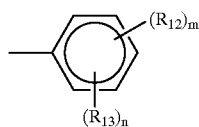

(VI)

in which $R_{12}$ is an alkyl group from $C_1$ to $C_5$, partially or totally fluorinated;

$R_{13}$ is selected from the group consisting of alkyl and alkoxy groups from $C_1$ to $C_4$, —$SiR_4R_5R_6$, halide, —$SO_3M$, —$CO_2M$, —$PO_3M$, —$NR_7R_8$ and —$[^+NR_7R_8R_9]Y^-$; m is an integer from 1 to 3 ; n is 0 or an integer from 1 to 4, the sum of m+n being from 1 to 5;

$R_4$, $R_5$ and $R_6$ are, independently from each other, selected from the group consisting of alkyl groups from $C_1$ to $C_{12}$ and phenyl groups; $R_7$ and $R_8$, taken separately, are each selected from the group consisting of hydrogen, alkyl groups from $C_1$ to $C_{12}$ and phenyl groups, or, taken together, represent a group selected from the group consisting of tetramethylene, pentamethylene and 3-oxa-1,5-pentylene; and $R_9$ is hydrogen or an alkyl group from $C_1$ to $C_4$;

M is hydrogen or an alkali metal; and Y is the anion of a monobasic acid; or

B. Z is nitrogen, $R_1$ is selected from the group consisting of alkyl groups from $C_1$ to $C_8$ and phenyl groups, optionally substituted by 1 to 3 substitutents selected from the group consisting of alkyl and alkoxy groups from $C_1$ to $C_4$, $R_2$ and $R_3$ are, independently from each other, selected from the group consisting of alkyl groups from $C_1$ to $C_{12}$, cycloalkyl groups from $C_5$ to $C_{12}$ and phenyl groups optionally substituted by 1 to 3 alkyl groups from $C_1$ to $C_4$; or $R_2$ and $R_3$ are taken together with the nitrogen to form a 5 to 12-membered ring, optionally comprising further nitrogen or oxygen atoms; and $R_{10}$ and $R_{11}$ are each a phenyl group.

Ligands which are preferred in the context of the present invention are those represented by the general formula

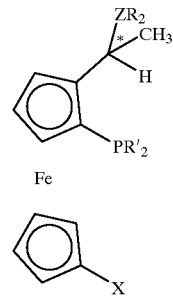

(VIII)

Fe
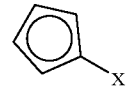

in which the carbon atom marked by the asterisk is an asymmetric carbon atom, X is hydrogen or a bridging group bonded to a polymer as defined above, Z is a phosphorous atom, and R and R' are independently from each other selected from the group consisting of linear and branched alkyl groups from $C_1$ to $C_4$, a cyclohexyl group and phenyl groups which are optionally substituted by 1 to 3 alkyl groups from $C_1$ to $C_4$, which alkyl groups may be partially or entirely fluorinated; or wherein Z is a nitrogen atom and R and R' are independently from each other selected from the group consisting of linear and branched alkyl groups from $C_1$ to $C_4$, a cyclohexyl group, and phenyl groups which are optionally substituted by 1 to 3 alkyl groups from $C_1$ to $C_4$.

Amongst the ligands defined by the above formula (VIII), those in which

Z=P and R=tert-butyl, R'=phenyl; R=R'=cyclohexyl; R≠R'=cyclohexyl, phenyl; R=tert-butyl, R'=p-$CF_3$-phenyl; R=cyclohexyl, R'=p-$CF_3$-phenyl; and R=cyclohexyl, R'=p-tolyl are preferred.

Likewise, the ligands of formula (VIII) in which $ZR_2$ is a $N(CH_3)_2$ group and R' is a phenyl group are preferred.

In one embodiment of the present invention, the ligands of formulae (V) and (VIII) are not immobilized, in which case X is hydrogen. A detailed description of this ligand type and its preparation is found in patent applications EP-A-564 406, 612 758 and 646 590. The ligands described therein are appropriate for a use in the present invention. The disclosure of these documents with respect to these ligands and their preparation is an integral part of the present invention and is incorporated by reference in the present application.

In a further embodiment of the present invention, there will be used an immobilized ligand. These ligands carry a group X which is a bridging group bonded to a polymer as mentioned in the above formulae (V) and (VIII). A definition for the said group X will be given in the following formula (IX). For reasons of clearness, there will be given the most general formula of the ligands in immobilized form corresponding to the ligands defined in the general formula (V). The definition will not be repeated for the ligands which have been cited above as being preferred and in which the group X will have the significations defined below.

The immobilized ligands which are used in the present invention are those according to the general formula

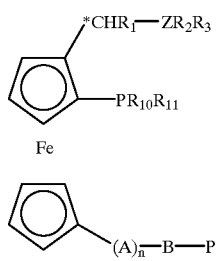

in which the symbols Z and $R_1$, $R_2$, $R_3$, $R_{10}$ and $R_{11}$ have the significations given above, n=0 or 1, A is an appropriate spacer group containing at least one atom chosen from the group consisting of oxygen, sulfur, silicon, nitrogen and carbon, B is a linking group between the cyclopentadienyl rest and the polymer P when n=0, or between A and P when n=1, and P is an organic or inorganic polymer.

In a preferred embodiment with respect to the use of the immobilized ligands of formula (IX),
n is 0 and B is a group of formula

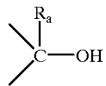

in which R is a hydrogen atom or an alkyl group from $C_1$ to $C_4$; or b) n=1 and A is a group of formula $-[Si(R_{14}R_{15})]_m R_{16}-$, in which m is 0 or 1, the groups $R_{14}$ and $R_{15}$ can be identical or different and represent independently from each other a substituent selected from the group consiting of alkyl groups from $C_1$ to $C_{12}$, cycloalkyl groups from $C_3$ to $C_7$, benzyl groups and phenyl groups or, taken together, represent an alkylene group from $C_5$ to $C_{12}$, and $R_{16}$ represents a substituent selected from the group consisting of a phenylene group, unsubstituted alkyl groups from $C_1$ to $C_{12}$ and alkyl groups from $C_1$ to $C_{12}$ substituted by at least one atom selected from the group consisting of halides and hydroxy groups, and B is a group of formula $N(R_{17})-C(O)-N(H)-(CH_2)_o-Si(R_{18})_{3-p}-(O)_p-$ or of formula $-O-C(O)-N(H)(CH_2)_o-Si(R_{18})_{3-p}-(O)_p-$, in which $R_{17}$ is hydrogen or an alkyl group from $C_1$ to $C_{12}$, o is an integer from 1 to 12, $R_{18}$ is an alkyl group from $C_1$ to $C_4$ or an alkoxy group from $C_1$ to $C_{12}$ and p is an integer from 1 to 3, and P is silica; or c) n=1 and A is a group of formula $-[Si(R_{14}R_{15})]_m R_{16}-$, in which m is 0 or 1, the groups $R_{14}$ and $R_{15}$ can be identical or different and represent independently from each other a substituent selected from the group consiting of alkyl groups from $C_1$ to $C_{12}$, cycloalkyl groups from $C_3$ to $C_7$, benzyl groups and phenyl groups or, taken together, represent an alkylene group from $C_5$ to $C_{12}$, and $R_{16}$ represents a substituent selected from the group consisting of a phenylene group, unsubstituted alkyl groups from $C_1$ to $C_{12}$ and alkyl groups from $C_1$ to $C_{12}$ substituted by at least one atom selected from the group consisting of halides and hydroxy groups, and B is selected from the group consisting of i) the groups of formulae $N(R_{17})-C(O)-$, $N(R_{17})-C(O)-N(H)-R_{19}-N(H)-C(O)-$ and $-O-C(O)-N(H)-R_{19}-N(H)-C(O)-$, in which $R_{17}$ has the sense given above, $R_{19}$ is a bridging group derived from a diisocyanate selected from the group consisting of substituted and unsubstituted alkylene groups from $C_2$ to $C_{20}$, and substituted and unsubstituted phenylene, naphthylene and biphenylene groups, ii) groups capable of reacting with the monomers forming the polymer P by polymerization or copolymerization, and iii) groups capable of reacting with the polymer P or with functional groups present on said polymer P, and P is a functionalized or non-functionalized organic polymer.

Non-limiting examples for organic polymer which can be used in the context of the present invention include polyolefines, polyacrylates, polyisoprenes, polybutadienes, polystyrenes, polyphenylenes, polyvinylchloride, polyvinylidene chloride, polyallyl polymers, polyurethanes, polyethers, polyesters and polyamides. If necessary, the polymers may be functionalized. As is evident from the foregoing, the group B may react with the respective monomer of the polymer P by polymerization or copolymerization, and the immobilized ligands will thus be obtained by mixing the monomer and the non-immobilized ligand carrying an appropriate group B and subjecting the said mixture to polymerization conditions which are known to a person skilled in the art. It is also possible to use polymers P carrying functional groups which react with appropriate groups B to give the immobilized ligands used in the present invention. Said functional groups may be groups which are present as such on the polymer, or groups introduced by functionalization of the polymer. Appropriate polymers, functionalized or non-functionalized, and groups B are known to a person skilled in the art.

The ligands of formula (IX) are the object of the patent applications EP-A-729 969 and WO 98/01457. The content of the above-cited applications concerning appropriate polymers and groups which link these polymers to the cyclopentadienyl rest (designated above by A and B) is an integral part of the present invention and is incorporated by reference.

The said phosphorous ligand can also be a ligand as defined by the general formula

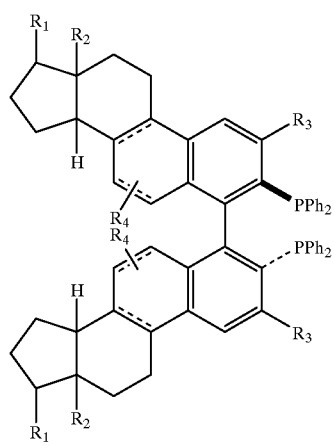

Ph = phenyl in which $R_1$ is selected from the group consisting of hydrogen, fluoride, alkyl groups, acyl groups, and a group of formula $XR_5$ in which X is oxygen or sulfur and $R_5$ is selected from the group consisting of hydrogen, alkyl groups and aryl groups;

$R_2$ is selected from the group consisting of hydrogen and alkyl groups, with the stereochemistry of the $C_{-13}$, $C_{-14}$ and $C_{-17}$ being α or β;

$R_3$ is selected from the group consisting of hydrogen, fluoride, alkyl groups, aryl groups, trialkylsilyl groups and a group of formula $XR_6$ in which X has the sense indicated above and $R_6$ is selected from the group consisting of hydrogen, alkyl groups, aryl groups and trifluoromethylsulfonyl groups;

$R_4$ is a substituent in position 6 or 7 of the steroide and is selected from the group consisting of hydrogen, fluoride, alkyl groups, aryl groups and a group of formula $YR_7$ in which Y is oxygen, sulfur or a trialkylsilyl group and $R_7$ is selected from the group consisting of hydrogen, alkyl groups, aryl groups and a trifluoromethylsulfonyl group; the B cycle of the steroide being saturated or carrying two double bonds.

In a preferred embodiment of the present invention, the ligand represented by the above general formula (X) is a ligand of formula

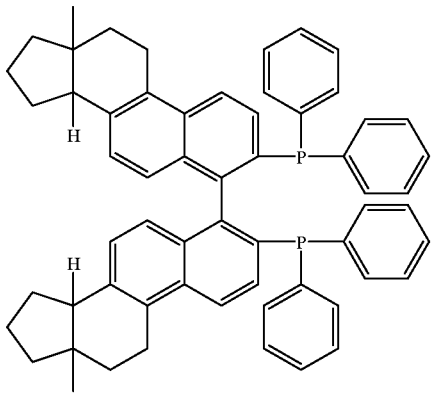

(XI)

or 4,4'-Bis(diphenylphosphino-13-estra-1,3,5(10),6,8,-pentaene).

The diphosphine ligands as represented by the above formula (XI) are described in detail in the patent application EP-A-849 274. The content of this application with respect to the ligands disclosed therein is an integral part of the present invention and is incorporated by reference in the present application.

All the above-cited references mention the use of the respective ligand type in metal catalysts which are useful for the hydrogenation of various substrates containing olefinic or carbon-nitrogen double bonds. However, there is no mention or hint in these documents that metal catalysts carrying the above-mentioned ligands may find use in applications other than those cited, in particular the isomerization of allyl substrates, which is the object of the present invention.

It should be mentioned that it was particularly surprising to find a catalytic activity for metal complexes carrying the ligands of the above formula (V) in which Z is a nitrogen atom because this is the first example ever for the use of a ligand of such structure in the isomerization reaction which is the object of the present invention. To the best of our knowledge, all ligands used up to now were bidentate diphosphine ligands, and there cannot be found in the prior art any example for the use of such ligands in in catalysts useful for the isomerization of compounds (I).

Now, these nitrogen-containing ligands allow to obtain metal catalysts which form another preferred embodiment of the present invention and due, on the one hand, to the easy recuperation of the ligand after complete reaction. The said recuperation can be carried out by precipitation of the ligand using an appropriate acid. On the other hand, the said nitrogen-containing acids are useful as starting products for the synthesis of the diphosphines of formula (V) in which Z is a phosphorous atom, and they are therefore also advantageous from an economical point of view.

As metal complexes which serve as catalyst for the isomerization reaction in the context of the present invention, there will be used Rh-, Ir- and Ru-complexes, preferably Rh-complexes.

The synthesis of the active rhodium complexes is known the person skilled in the art. This synthesis includes the reaction of the chiral phosphines according to the above formulae with an appropriate precursor complex of Rh(I). As non-limiting examples, there should be cited the complexes of the type $[Rh(ene)_2Y]_2$ or $[Rh(diene)Y]_2$, which react with the mentioned phosphorous ligands in presence of a silver salt of the general formula AgX, or the complexes of the type $[Rh(diene)_2]X$, which likewise react with phosphorous ligands to give the catalytical active complexes of the invention. If necessary, the synthesis of the active complexes is carried out using hydrogen, under pressure 5 which may reach 100 bar, preferably up to 40 bar. The active complexes can be described by the general formulae $[RhL^*(ene)_2]^+X^-$, $[RhL^*(diene)]^+X^-$, $[RhL^*]^+X^-$ or $[RhL^*_2]^+X^-$. In these formulae, L* is a chiral phosphine ligand as defined in any of the formulae (V), (IX) or (X) as defined above, ene is an olefin such as, for example, ethylene, propylene or butene, diene is a diene such as, for example, 1,3-butadiene, 1,3-pentadiene, cyclopentadiene, 1,5-hexadiene, 1,4-cyclohexadiene, 1,4- or 1,5-heptadiene, 1,4- or 1,5-cyclcoheptadiene, 1,4- or 1,5-octadiene, 1,4- or 1,5-cyclooctadiene, or norbomadiene. Preferred dienes are 1,5-cyclooctadiene (COD) and norbomadiene (NBD). $X^-$ is an appropriate anion such as, for example, a halide, $Cl_4^-$, $BF_4^-$, $B(C_6H_5)_4^-$, $PF_6^-$, $PCl_6^-$, $CH_3COO^-$, $CF_3COO^-$; $SbF_6^-$, $AsF_6^-$, $CH_3SO_3^-$, $FSO_3^-$ or $CF_3SO_3^-$, and Y is a bridging anione selected from halides.

We could obtain particularly advantageous results when the triflate anion $CF_3SO_3^-$ was used as counter ion for the active complexes in the context of the present invention. In many cases the use of this anion did not only give the highest conversions and enantiomeric excesses (ee) with respect to the anions described and used until now in the type of isomerization which is the object of the present application. In some embodiments, its use also allowed to employ lower amounts of catalyst with respect to the substrate than with other counterions. This effect will become more evident from the examples below.

The iridium complexes which can be used in the process of the invention are synthesized from a phosphine ligand and an appropriate precursor complex, in a way similar to the rhodium complexes. Non-limiting examples for appropriate precursor complexes include $[Ir(COD)Y]_2$, $IrY_3$, $[IrY_6]^{2-}$, wherein COD is 1,5-cyclooctadiene and Y is a bridging anion selected from the halides. With respect to ruthenium, several complexes of this metal are known which are appropriate as precursor complex in the process according to the present invention. Non-limiting examples include $[Ru_2(ACOO)_4(H_2O)(diene)_2]$(A=substituted or unsubstituted alkyl or aryl group or halide), $[RuY_2(aryl)]_2$ (aryl=aryl groupe such as, for example, benzene, toluene, cymene, Y=bridging anion selected from the group consisting of halides).

A large number of prochiral allyl amines of the above formula (I) and which can be used as substrate in the process of the invention are known to the person skilled in the art. There is made reference to the allylamines which are cited in the patent EP-B-068 506, page 4, lines 1–7, respectively the prochiral amines cited in this passage, which are incorporated by reference in the present application.

Preferred substrates for the isomerization reaction according to the invention are diethylnerylamine and diethylgeranylamine, as well as cyclohexylgeranylamine, methylcyclohexylgeranylamine and (E)- and (Z)-N,N-diethyl-7-hydroxy-3,7-dimethyl-2-octenylamine [see K. Tani, Pure Appl. Chem. 1985, (57), 1845 and J. Am. Chem. Soc. 1984 (106) 5208]. The process according to the invention allows to obtain optically active citronellal, after hydrolysis of the chiral enamine formed in the process of the invention.

The process according to the present invention allows to isomerize chiral allyl amines with conversions which can reach 100% and enantiomeric excesses of higher than 90%, often close to 100%. The result depends on the complex and the phosphine used, as well as on the reaction conditions, such as, for example, temperature, amount of catalyst with respect to the substrate, etc. The person skilled in the art will ajust these parameters in order to obtain the optimum result of the reaction.

When the process of the invention is carried out, the active complex may be synthesized beforehand, ex situ, and then added to the reactor, or be formed in situ, from a precursor complex as described above and the chosen chiral phosphine.

The quantity of catalyst with respect to the substrate can vary within the range from about 0.05 mole % to about 20 mole %. Preferably, the catalyst will be used in a proportion from about 0.1 to about 5 mole % with respect to the substrate. The catalyst may be used several times; after the end of the isomerization reaction, the catalyst will be separated from the reaction medium, e.g. by distillation of the latter, and new substrate will be added. This operation can be repeated several times without pronounced desactivation of the catalyst.

When in the isomerization reaction according to the present invention ligands fixed on polymers, e.g. those according to the general formula (IX), will be used, a separation of the catalyst from the reaction mixture is particularly easy, because such separation can be carried out by simple decantation, without a distillation being necessary. After the separation of the reaction mixture, the ctalyst can be reused in the isomerization reaction, and only a very weak desactivation of the catalyst is observed, even after several repeated runs of the process with the same catalyst.

The best results were obtained when the solvent used was selected from the group consisting of alcohols such as, for example, ethanol, esters such as, for example, ethyl acetate, and tetrahydrofuran (THF). The above-mentioned solvents are prefered in the context of the present invention, with THF giving the best results.

The isomerization reaction can be carried out at temperatures ranging from about 0° C. to about 150° C., preferably from about 40° C. to about 110° C. The best temperature will be chosen as a function of the substrate and the solvent used, which is a routine work for the person skilled in the art.

The invention will now be illustrated in greater detail in the following examples in which the temperatures are indicated in degrees Celsius and the abreviation have the usual meaning in the art.

EMBODIMENTS OF THE INVENTION

A. Preparation of Starting Products

The allyl amines of formula (I) are commercially available products. The diethylgeranylamine used (origin: Dérivés Résiniques et Terpéniques, Castets, France) had a purity from 94–99% as determined by gas chromatographie, and the diethylnerylamine used had a purity of 95% and was prepared as described by K. Takabe, Y. Yamada, T. Katagiri, J. Tanaka in Org. Synth. 1988, (67), 48. The phosphine ligands were obtained from Novartis AG, Basle, Switzerland, Schering AG, Berlin, Germany, or from current speciality suppliers. The precursor complexes for the active complexes of the invention can be synthesized in a manner known to the person skilled in the art, or as described in the references EP-A-398 132, EP-A-643 065 or WO 95/21176.

B. General Procedure for the Isomerization Process of Diethylgeranylamine and Diethylnerylamine I. Precursor complex: $[Rh(COD)_2]^+X^-$ (X=anion as defined above) In a glove box, a solution of 0.025 mmole of the respective precursor complex (for example $[Rh(COD)_2]^+$ $SO_3CF_3^-$) in 2.5 ml of THF (0.01 M) was added to 0.025 mmole of the respective ligand in a one-necked flask equipped with a stopcock. The solution was stirred for 1 h, then a solution of 10 mmole of diethylgeranylamine or diethylnerylamine in 10 ml of the respective solvent was added. The flask was then equipped with a reflux condenser connected to a Schlenk line, the apparatus was purged with argon and the solution brought to reflux. Reaction temperature was held constant during the reaction time indicated in the table. The mixture was then cooled to 0° C. before adding 5 ml of a 1:4 of acetic acid/water. The reaction mixture was raised to room temperature and the solution extracted with diethyl ether. The extract was washed with water (10 ml), 15% NaOH solution (2×10 ml), then neutralized with water and thereafter dried over $MgSO_4$. After concentration of the resulting solution, the residue was distilled in a bulb-to-bulb apparatus to give optically active citronellal and with the conversions and ee's as indicated in the tables below.

II. Precursor complex: $[Rh(COD)Y]_2$ (Y=anion as defined above) In a glove box, a solution of 0.025 mmole of the respective precursor complex (for example [Rh(COD) Cl]$_2$ in 5 ml of THF (0.005 M) was added to 0.055 mmole of the respective ligand and 0.19 mmole of the respective silver salt AgX in a flask. The solution was stirred for 1 h and then transferred via a syringe, and under filtration through an Acrodisk® filter into a one-necked flask equipped with a stopcock. The reaction was then continued as described above under I.

III. Precursor complex: $[Rh(COD)_2]^+X^-$ (X=anion as defined above) and hydrogen treatment after addition of the substrate In a glove box, a solution of 0.025 mmole of the respective precursor complex (for example $[Rh(COD)_2]^+$ $BF_4$) in 2.5 ml of THF (0.01 M) was added to 0.025 mmole of the respective ligand in a one-necked flask equipped with a stopcock. The solution was stirred for 1 h, then a solution of 10 mmole of diethylgeranylamine or diethylnerylamine in 10 ml of the respective solvent was added. The flask was then equipped with a reflux condenser connected to a Schlenk line, the apparatus was purged with hydrogen and then with argon. The solution was brought to reflux for the appropriate reaction time. The thus-obtained solution was then cooled, 5 ml of pentane were added and the mixture obtained was filtered using a syringe through an Acrodisk® filter. Workup was continued as described above under I.

IV. Precursor complex: $[Rh(COD)_2]^+X^-$ (X=anion as defined above) and hydrogen treatment before addition of the substrate In a glove box, a solution of 0.025 mmole of the respective precursor complex (for example $[Rh(COD)_2]^+$ $BF_4$) in 2.5 ml of THF (0.01 M) was added to 0.025 mmole of the respective ligand in a one-necked flask equipped with a stopcock. The solution was stirred for 1 h. The flask was then equipped with a reflux condenser connected to a Schlenk line, and was then purged with hydrogen and then with argon. Then a solution of 10 mmole of diethylgeranylamine or diethylnerylamine in 10 ml of the respective solvent was added. The solution was brought to reflux for the appropriate reaction time. The thus-obtained solution was then cooled, 5 ml of pentane were added and the mixture obtained was filtered using a syringe through an Acrodisk® filter. Workup was continued as described above under I.

C. Examples for the Use of Specific Ligands for the Isomerization of Diethylgeranylamine and Diethylnerylamine General Remark In the tables below, the conversions and enatiomeric excesses (ee) are always given with respect to the citronellal obtained after hydrolysis of the enamine formed. The isolation of the enamine as well as its hydrolysis are carried out by methods which are known to a person skilled in the art and which are, for example, described in the above-cited patent EP-B-068 506. (+/−) indicates if the citronellal which was formed in a preponderant amount was in the form of the (+) or (−) isomer. The ee's were determined by gas chromatographie on a column of the type Brechbuehler SA, # 27425-025 having a length of 25 m and a diameter of 0.25 mm. Unless not indicated otherwise, the precursor complex and the ligand were always used in a cencentration of 1 mole % with respect to the substrate. In the same column of the table, the numbers I–IV indicate if the reaction had been carried out according to mode I, II, III or IV described above under B.

EXAMPLE 1

Ligand Used (+)-(S)-N,N-dimethyl-1-[(R)-2-(diphenylphosphino)ferrocenyl]ethylamine of formula

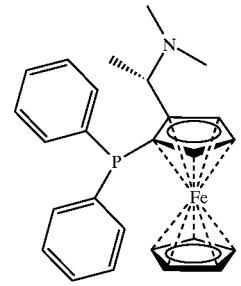

The process was carried out as described above under B, using the precursor complexes cited in the Table I in which are given results of the reactions.

TABLE I

| | | | substrate: diethylgeranylamine | | | | | | | |
|---|---|---|---|---|---|---|---|---|---|---|
| Run | Embodiment | Precursor complex | Complexation time | Hydrogenation time | Reaction time | Temp. | Conversion | ee | (+/−) | Solvent |
| A | I | [(COD)$_2$Rh]BF$_4$ | 01:00 | — | 18:00 | 66° C. | 33% | 88% | (+) | THF |
| B | IV | [(COD)$_2$Rh]BF$_4$ | 02:30 | 01:00 | 18:00 | 66° C. | 79% | 88% | (+) | THF |

EXAMPLE 2

Ligand Used (S)-1-[1-(R)-2-(dicyclohexylphosphino)ferrocenyl]ethyldicyclohexylphosphine of formula

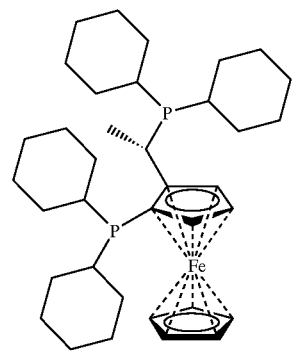

The process was carried out as described above under B, using the precursor complexes cited in the Table II in which are given the results of the reactions.

TABLE II substrate: diethylgeranylamine

| Run | Embodiment | Precursor complex | complexation time | Hydrogenation time | Reaction time | Temp. | Conversion | ee | (+/−) | Solvent |
|---|---|---|---|---|---|---|---|---|---|---|
| A | I | [(COD)$_2$Rh]BF$_4$ | 01:00 | — | 18:00 | 66° C. | 33% | 88% | (+) | THF |
| B | I | [(COD)$_2$Rh]BF$_4$ | 01:00 | — | 20:00 | 81° C. | 23% | 73% | (+) | CHex |
| C | I | [(COD)$_2$Rh]BF$_4$ | 01:00 | — | 20:00 | 77° C. | 29% | 79% | (+) | EtOAc |
| D | I | [(COD)$_2$Rh]SO$_3$CF$_3$ | 01:00 | — | 22:00 | 66° C. | 81% | 89% | (+) | THF |
| E | I/0.5 mole % of catalyst | [(COD)$_2$Rh]SO$_3$CF$_3$ | 01:00 | — | 22:00 | 66° C. | 72% | 89% | (+) | THF |
| F | I/0.25 mole % of catalyst | [(COD)$_2$Rh]SO$_3$CF$_3$ | 01:00 | — | 70:00 | 66° C. | 33% | 86% | (+) | THF |
| G | III | [(COD)$_2$Rh]BF$_4$ | 02:30 | 01:00 | 18:00 | 66° C. | 79% | 88% | (+) | THF |
| H | III | [(COD)$_2$Rh]SO$_3$CF$_3$ | 01:00 | 01:30 | 18:00 | 66° C. | 99% | 88% | (+) | THF |
| I | III/2 eq. of ligand | [(COD)$_2$Rh]SO$_3$CF$_3$ | 01:00 | 01:00 | 18:00 | 66° C. | 100% | 86% | (+) | THF |

CHex = cyclohexane
EtOAc = ethyl acetate

EXAMPLE 3

Ligand Used (R)-1-[1-(S)-2-(diphenylphosphino)ferrocenyl]ethyldicyclohexylphosphine of formula

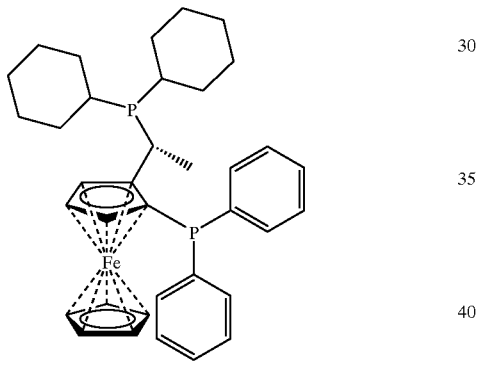

The process was carried out as described above under B, using the precursor complexes cited in the Table III in which are given the results of the reactions.

TABLE IIIA (substrate: diethylgeranylamine)

| Run | Embodiment | Precursor complex/silver salt | Complexation time | Hydrogenation time | Reaction time | Temp. | Conversion | ee | (+/−) | Solvent |
|---|---|---|---|---|---|---|---|---|---|---|
| A | I | [(COD)$_2$Rh]BF$_4$ | 01:00 | — | 18:00 | 66° C. | 71% | 76% | (−) | THF |
| B | I | [(COD)$_2$Rh]BF$_4$ | 01:00 | — | 20:00 | 77° C. | 20% | 69% | (−) | EtOAc |
| C | I | [(COD)$_2$Rh]SO$_3$CF$_3$ | 01:00 | — | 21:00 | 66° C. | 100% | 74% | (−) | THF |
| D | I | [(COD)$_2$Rh]BF$_4$ | 01:00 | — | 21:00 | 78° C. | 41% | 67% | (−) | EtOH |
| E | I | [(COD)$_2$Rh]SO$_3$CF$_3$ | 01:00 | — | 21:00 | 78° C. | 70% | 64% | (−) | EtOH |
| F | I/0.5 mole % of catalyst | [(COD)$_2$Rh]SO$_3$CF$_3$ | 01:00 | — | 22:00 | 66° C. | 99% | 74% | (−) | THF |
| G | I/0.2 mole % of catalyst | [(COD)$_2$Rh]SO$_3$CF$_3$ | 01:00 | — | 20:00 | 66° C. | 100% | 76% | (−) | THF |
| H | II | [(COD)RhCl]$_2$-AgClO$_4$ | 01:00 | — | 20:00 | 66° C. | 99% | 72% | (−) | THF |
| I | II | [(COD)RhCl]$_2$-AgSO$_3$CF$_3$ | 01:00 | — | 21:00 | 66° C. | 98% | 73% | (−) | THF |
| J | II | [(COD)RhCl]$_2$- | 03:00 | — | 19:00 | 66° C. | 98% | 79% | (−) | THF |

TABLE IIIA-continued (substrate: diethylgeranylamine)

| Run | Embodiment | Precursor complex/silver salt | Complexation time | Hydrogenation time | Reaction time | Temp. | Conversion | ee | (+/−) | Solvent |
|---|---|---|---|---|---|---|---|---|---|---|
| K | II | [(COD)RhCl]$_2$-AgPF$_6$ | 05:00 | — | 18:00 | 66° C. | 98% | 80% | (−) | THF |
| L | II | [(COD)RhCl]$_2$-AgPF$_6$ | 03:00 | — | 19:00 | 66° C. | 70% | 77% | (−) | THF |
| M | II | [(COD)RhCl]$_2$-AgSbF$_6$ | 05:00 | — | 18:00 | 66° C. | 66% | 77% | (−) | THF |
| N | II/0.5 mole % of ligand | [(COD)RhCl]$_2$-AgSbF$_6$ | 01:00 | — | 20:00 | 66° C. | 98% | 85% | (−) | THF |
| O[1)] | II/0.5 mole % of ligand | [(COD)RhCl]$_2$-AgPF$_6$ | 01:00 | — | 20:00 | 66° C. | 99% | 90% | (−) | THF |
| P | IV | [(COD)$_2$Rh]BF$_4$ | 01:00 | 00:15 | 18:00 | 66° C. | 98% | 74% | (−) | THF |
| Q | II | [(COD)$_2$Rh]SO$_3$CF$_3$ | 01:00 | 00:30 | 22:00 | 66° C. | 100% | 67% | (−) | THF |
| R | III/2 eq. of ligand | [(COD)$_2$Rh]SO$_3$CF$_3$ | 01:00 | 01:30 | 18:00 | 66° C. | 97% | 75% | (−) | THF |
| S | III/2 eq. of ligand | [(COD)RhCl]$_2$-AgPF$_6$ | 01:00 | 00:15 | 18:00 | 66° C. | 100% | 88% | (−) | THF |

[1)]solvent dried over molecular sieves
EtOH = ethanol
EtOAc = ethyl acetate

TABLE IIIB (substrate: diethylnerylamine)

| Run | Embodiment | Precursor complex/silver salt | Complexation time | Hydrogenation time | Reaction time | Temp. | Conversion | ee | (+/−) | Solvent |
|---|---|---|---|---|---|---|---|---|---|---|
| A | I/0.25 mole % of catalyst | [(COD)$_2$Rh]SO$_3$CF$_3$ | 01:00 | — | 20:00 | 66° C. | 100% | 86% | (+) | THF |

EXAMPLE 4

Ligand Used (R)-1-[1-(S)-2-(di-p-tolylphosphino)ferrocenyl]ethyldicyclohexylphosphine of formula

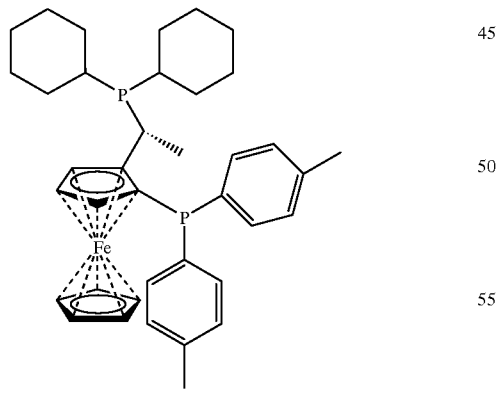

The process was carried out as described above under B, using the precursor complexes cited in the Table IV in which are given the results of the reactions.

TABLE IV substrate: diethylgeranylamine

| Run | Embodiment | Precursor complex/silver salt | Complexation time | Hydrogenation time | Reaction time | Temp. | Conversion | ee | (+/−) | Solvent |
|---|---|---|---|---|---|---|---|---|---|---|
| A | I | [(COD)$_2$Rh]SO$_3$CF$_3$ | 01:00 | — | 22:00 | 66° C. | 98% | 75% | (−) | THF |
| B | IV | [(COD)RhCl]Cl]$_2$-AgPF$_6$ | 01:00 | — | 20:00 | 66° C. | 100% | 75% | (−) | THF |

EXAMPLE 5

Ligand Used (R)-1-[1-(S)-2-(di-p-trifluoromethylphosphino)ferrocenyl]ethyldicyclo-hexylphosphine of formula

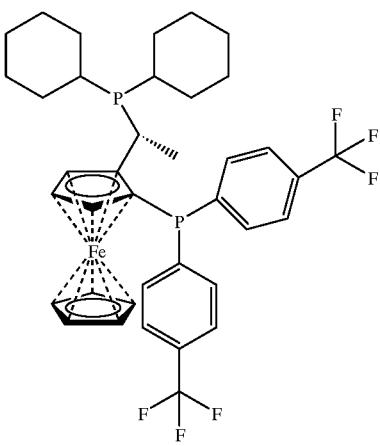

The process was carried out as described above under B, using the precursor complexes cited in the Table V in which are given the results of the reactions.

EXAMPLE 6

Ligand Used (R)-1-[1-(S)-2-(diphenylphosphino)ferrocenyl]ethyl-di-tert-butylphosphine of formula

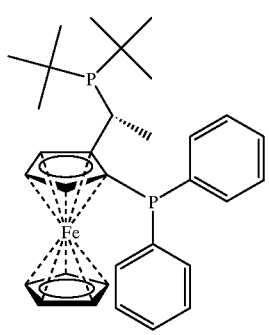

The process was carried out as described above under B, using the precursor complexes cited in the Table VI in which are given the results of the reactions.

TABLE V substrate: diethylgeranylamine

| Run | Embodiment | Precursor complex/silver salt | Complexation time | Hydrogenation time | Reaction time | Temp. | Conversion | ee | (+/−) | Solvent |
|---|---|---|---|---|---|---|---|---|---|---|
| A | I | [(COD)$_2$Rh]SO$_3$CF$_3$ | 01:00 | — | 22:00 | 66° C. | 94% | 79% | (−) | THF |
| B | IV | [(COD)RhCl]$_2$-AgPF$_6$ | 01:00 | — | 20:00 | 66° C. | 47% | 86% | (−) | THF |

TABLE VIA (substrate: diethylgeranylamine)

| Run | Embodiment | Precursor complex/silver salt | Complexation time | Hydrogenation time | Reaction time | Temp. | Conversion | ee | (+/−) | Solvent |
|---|---|---|---|---|---|---|---|---|---|---|
| A | I | [(COD)$_2$Rh]BF$_4$ | 01:00 | — | 18:00 | 66° C. | 43% | 90% | (−) | THF |
| B | I | [COD)$_2$Rh]BF$_4$ | 01:00 | — | 20:00 | 77° C. | 93% | 80% | (−) | EtOAc |
| C | I | [(COD)$_2$Rh]SO$_3$CF$_3$ | 01:00 | — | 21:00 | 66° C. | 99% | 83% | (−) | THF |
| D | I/0.5 mole % of catalyst | [(COD)$_2$Rh]SO$_3$CF$_3$ | 01:00 | — | 22:00 | 66° C. | 99% | 89% | (−) | THF |
| E | I/0.25 mole % of catalyst | [(COD)$_2$Rh]SO$_3$CF$_3$ | 01:00 | — | 70:00 | 66° C. | 99% | 92% | (−) | THF |
| F | II | [(COD)RhCl]$_2$-AgClO$_4$ | 01:00 | — | 20:00 | 66° C. | 98% | 89% | (−) | THF |
| G | II | [(COD)RhCl]$_2$-AgSO$_3$CF$_3$ | 01:00 | — | 21:00 | 66° C. | 99% | 72% | (−) | THF |
| H | II | [(NBD)RhCl]$_2$-AgSO$_2$CF$_3$ | 01:00 | — | 21:00 | 66° C. | 69% | 91% | (−) | THF |
| I | II | [(NBD)RhCl]$_2$-AgSO$_3$CF$_3$ | 05:00 | — | 18:00 | 66° C. | 67% | 92% | (−) | THF |
| J | II | [(NBD)RhCl]$_2$-AgPF$_6$ | 01:00 | — | 21:00 | 66° C. | 73% | 91% | (−) | THF |
| K | III | [(COD)$_2$Rh]SO$_3$CF$_3$ | 01:00 | 00:30 | 20:00 | 66° C. | 100% | 81% | (−) | THF |
| L | III/2 eq. of ligand | [(COD)$_2$Rh]SO$_3$CF$_3$ | 01:00 | 01:30 | 18:00 | 66° C. | 100% | 71% | (−) | THF |

EtOAc = ethyl acetate

TABLE VIB (substrate: diethylnerylamine)

| Run | Embodiment | Precursor complex/silver salt | Complexation time | Hydrogenation time | Reaction time | Temp. | Conversion | ee | (+/−) | Solvent |
|---|---|---|---|---|---|---|---|---|---|---|
| A | I/0.25 mole % of catalyst | [(COD)$_2$Rh]SO$_3$CF$_3$ | 01:00 | — | 20:00 | 66° C. | 100% | 97% | (+) | THF |

EXAMPLE 7

Ligand Used (R)-1-[1-(S)-2-(di-p-trifluoromethylphosphino)ferrocenyl]ethyl-di-tert-butylphosphine of formula

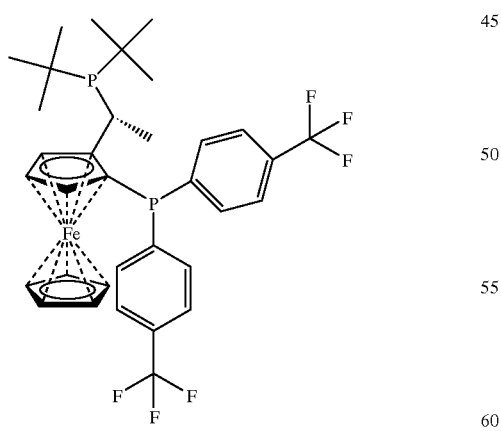

The process was carried out as described above under B, using the precursor complexes cited in the Table VII in which are given the results of the reactions.

TABLE VII substrate: diethylgeranylamine

| Run | Embodiment | Precursor complex/silver salt | Complexation time | Hydrogenation time | Reaction time | Temp. | Conversion | ee | (+/−) | Solvent |
|---|---|---|---|---|---|---|---|---|---|---|
| A | I | [(COD)$_2$Rh]SO$_3$CF$_3$ | 01:00 | — | 20:00 | 66° C. | 100% | 89% | (−) | THF |
| B | II | [(COD)RhCl]$_2$-AgPF$_6$ | 01:00 | — | 20:00 | 66° C. | 42% | 90% | (−) | THF |

EXAMPLE 8

Ligand Used (R)-1-[1-(S)-2-(dicyclohexylphosphino)ferrocenyl]ethyldiphenylphosphine of formula

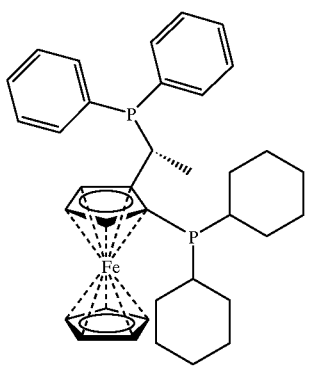

The process was carried out as described above under B, using the precursor complexes cited in the Table VIII in which are given the results of the reactions.

TABLE VIIIA (substrate: diethylgeranylamine)

| Run | Embodiment | Precursor complex/silver salt | Complexation time | Hydrogenation time | Reaction time | Temp. | Conversion | ee | (+/−) | Solvent |
|---|---|---|---|---|---|---|---|---|---|---|
| A | I | [(COD)$_2$Rh]BF$_4$ | 01:00 | — | 18:00 | 66° C. | 98% | 79% | (−) | THF |
| B | I | [(COD)$_2$Rh]SO$_3$CF$_3$ | 01:00 | — | 22:00 | 66° C. | 100% | 90% | (−) | THF |
| C | II | [(COD)RhCl]$_2$-AgPF$_6$ | 01:00 | — | 22:00 | 66° C. | 98% | 90% | (−) | THF |
| D | III | [(COD)$_2$Rh]BF$_4$ | 02:30 | 01:00 | 18:00 | 66° C. | 100% | 72% | (−) | THF |

TABLE VIIIB (substrate: diethylnerylamine)

| Run | Embodiment | Precursor complex/silver salt | Complexation time | Hydrogenation time | Reaction time | Temp. | Conversion | ee | (+/−) | Solvent |
|---|---|---|---|---|---|---|---|---|---|---|
| A | I/0.25 mole % of catalyst | [(COD)$_2$Rh]SO$_3$CF$_3$ | 1:00 | — | 20:00 | 66° C. | 100% | 93% | (+) | THF |

EXAMPLE 9

Ligand Used
(R)-1-[1-(S)-2-(diphenylphosphino)ferrocenyl]
ethyldicyclohexylphosphine fixed on silica of
formula

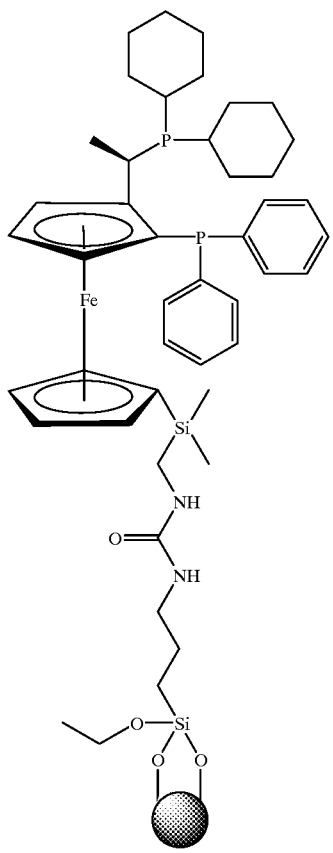

= SiO2

The process was carried out as described above under B, using the precursor complexes cited in the Table IX in which are given the results of the reactions.

EXAMPLE 10

Ligand Used
(R)-1-[1-(S)-2-(diphenylphosphino)ferrocenyl]ethyl-
di-tert-butylphosphine fixed on silica of formula

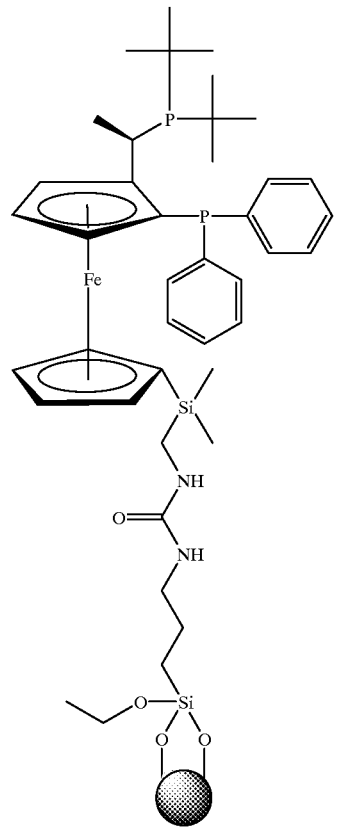

= SiO2

The process was carried out as described above under B, using the precursor complexes cited in the Table X in which are given the results of the reactions.

TABLE IX

| | | | substrate: diethylgeranylamine | | | | | | | |
|---|---|---|---|---|---|---|---|---|---|---|
| Run | Embodiment | Precursor complex/silver salt | Complexation time | Hydrogenation time | Reaction time | Temp. | Conversion | ee | (+/−) | Solvent |
| A | I | [(COD)$_2$Rh]SO$_3$CF$_3$ | 1:00 | — | 19:00 | 66° C. | 81% | 83% | (−) | THF |

TABLE X

| | | | substrate: diethylgeranylamine | | | | | | | |
|---|---|---|---|---|---|---|---|---|---|---|
| Run | Embodiment | Precursor complex/silver salt | Complexation time | Hydrogenation time | Reaction time | Temp. | Conversion | ee | (+/−) | Solvent |
| A | I | [(COD)$_2$Rh]SO$_3$CF$_3$ | 1:00 | — | 19:00 | 66° C. | 97% | 86% | (−) | THF |
| B | I/0.25 mole % of catalyst | [(COD)$_2$Rh]SO$_3$CF$_3$ | 1:00 | — | 19:00 | 66° C. | 97% | 87% | (−) | THF |

EXAMPLE 11

Ligand Used (R)-1-[1-(S)-2-(diphenylphosphino)ferrocenyl]
ethyldicyclohexylphosphine fixed on polystyrene of
formula

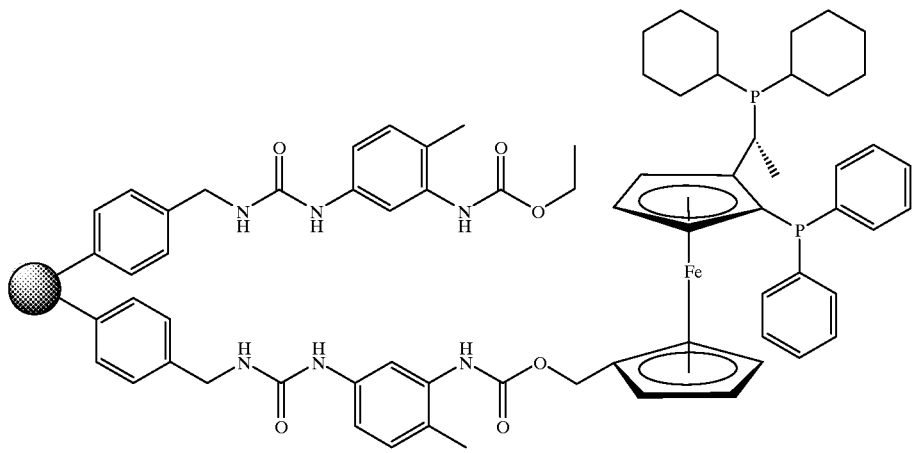

◯ = polystyrene

The process was carried out as described above under B, using the precursor complexes cited in the Table XI in which are given the results of the reactions.

TABLE XI

| | | | substrate: diethylgeranylamine | | | | | | | |
|---|---|---|---|---|---|---|---|---|---|---|
| Run | Embodiment | Precursor complex/silver salt | Complexation time | Hydrogenation time | Reaction time | Temp. | Conversion | ee | (+/−) | Solvent |
| A | I | [(COD)$_2$Rh]SO$_3$CF$_3$ | 1:00 | — | 19:00 | 66° C. | 54% | 78% | (+) | THF |

EXAMPLE 12

Ligands Used

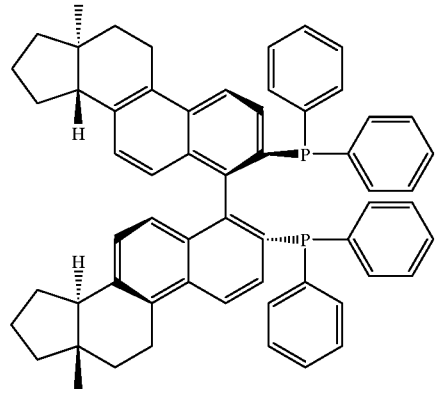

(Ra)-4-4'-bis(3-diphenylphosphino
estra-1,3,5(10)6,8-pentaene
"(R)-trans"

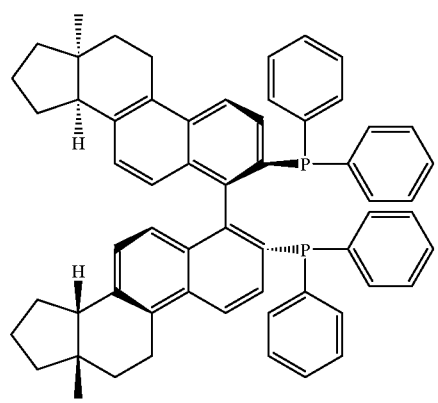

(Ra)-4-4'-bis(3-diphenylphosphino
13-epi-estra-1,3,5(10)6,8-pentaene
"(R)-cis"

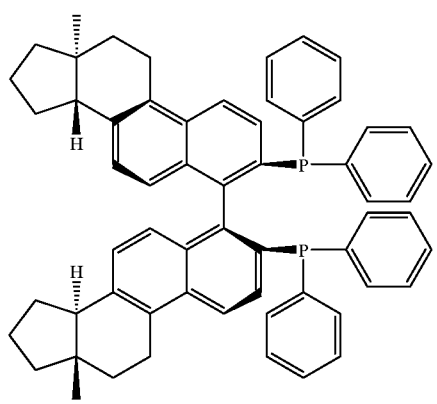

(Sa)-4-4'-bis(3-diphenylphosphino
13-epi-estra-1,3,5(10)6,8-pentaene
"(S)-cis"

The process was carried out as described above under B, using the precursor complexes cited in the Table XII in which are given the results of the reactions.

TABLE XIIA (substrate: diethylgeranylamine)

| Run | Embodiment | Precursor complex/silver salt | Complexation time | Hydrogenation time | Reaction time | Temp. | Conversion | ee | (+/−) | Solvent |
|---|---|---|---|---|---|---|---|---|---|---|
| A | I | [(COD)₂Rh]SO₃CF₃/ "(R)-trans" | 1:00 | — | 20:00 | 66° C. | 100% | 87% | (−) | THF |
| B | I | [(COD)₂Rh]SO₃CF₃/ "(R)-cis" | 1:00 | — | 20:00 | 66° C. | 100% | 93% | (−) | THF |
| C | I | [(COD)₂Rh]SO₃CF₃/ "(S)-cis" | 1:00 | — | 6:00 | 66° C. | 100% | 89% | (+) | THF |

TABLE XIIB

| | | | (substrate: diethylnerylamine) | | | | | | | |
|---|---|---|---|---|---|---|---|---|---|---|
| Run | Embodiment | Precursor complex/silver salt | Complexation time | Hydrogenation time | Reaction time | Temp. | Conversion | ee | (+/−) | Solvent |
| A | I | [(COD)$_2$Rh]SO$_3$CF$_3$/ "(R)-cis" | 1:00 | — | 20:00 | 66° C. | 100% | 95% | (+) | THF |

We claim:

1. Process for the stereospecific isomerisation of prochiral allylic systems represented by the formula

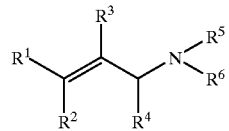

(I)

in which $R^1 \neq R^2$, each being selected from the group consisting of alkyl and alkenyl groups containing from 1 to 12 carbon atoms, aryl groups, optionally substituted by a hydroxy group, $R^3$ and $R^4$ are, independently from each other, selected from the group consisting of hydrogen, alkyl and alkenyl groups from $C_1$ to $C_{12}$ and aryl groups, $R^5$ is selected from the group consisting of hydrogen and alkyl and cycloalkyl groups containing from 1 to 8 carbon atoms, $R^6$ is selected from the group consisting of alkyl and cycloalkyl groups containing from 1 to 8 carbon atoms, or $R^5$ and $R^6$ are taken together with the nitrogen atom to form a ring selected from the group consisting of 5-membered rings, 6-membered rings and 6-membered rings which further contain an oxygen atom, into the group of compounds consisting of enamines as represented by the formula

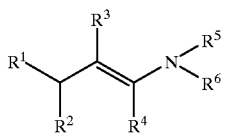

(II)

in which the symbols $R^1$–$R^6$ are as defined above, and imines as represented by the formula

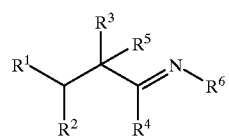

(III)

in which the symbols $R^1$–$R^4$ and $R^6$ are as defined above and $R^5$ is hydrogen, by means of catalysts selected from the group consisting of Rh, Ir and Ru compounds carrying at least one chiral phosphorous ligand, wherein said ligand is a compound represented by the formula (V)

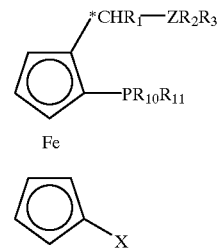

(V)

in which the carbon atom marked by an asterisk is an asymmetric carbon atom, X is hydrogen or a bridging group bonded to a polymer and represented by formula (A)$_n$—B—P in which n is 0 or 1, A is an appropriate spacer group containing at least one atom of oxygen, sulfur, silicon, nitrogen or carbon, B is a linking group between the cyclopentadienyl rest and the polymer P when n=0, or between A and P when n=1, and P is an organic or inorganic polymer, A. Z stands for a phosphorous atom; $R_1$ is selected from the group consisting of alkyl groups from $C_1$ to $C_8$, phenyl groups, optionally substituted by 1 to 3 alkyl or alkoxy groups from $C_1$ to $C_4$; $R_2$, $R_3$, $R_{10}$ and $R_{11}$ are, independently from each other, selected from the group consisting of alkyl groups from $C_1$ to $C_{12}$, cycloalkyl groups from $C_5$ to $C_{12}$, optionally substituted by an alkyl or alkoxy group from $C_1$ to $C_4$, and phenyl groups optionally carrying from 1 to 3 substituents selected from the group consisting of alkyl and alkoxy groups from $C_1$ to $C_4$, —SiR$_4$R$_5$R$_6$, halides, —SO$_3$M, —CO$_2$M, —PO$_3$M, —NR$_7$R$_8$ and —[$^+$NR$_7$R$_8$R$_9$]Y$^-$; or $R_2$, $R_3$, $R_{10}$ and $R_{11}$ represent, independently from each other, a group of formula

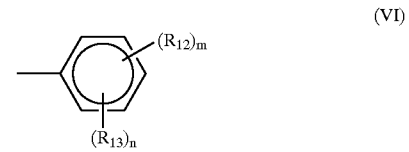

(VI)

in which $R_{12}$ is an alkyl group from $C_1$ to $C_5$, partially or totally fluorinated; $R_{13}$ is selected from the group consisting of alkyl and alkoxy groups from $C_1$ to $C_4$, —SiR$_4$R$_5$R$_6$, halide, —SO$_3$M, —CO$_2$M, —PO$_3$M, —NR$_7$R$_8$ and —[NR$_7$R$_8$R$_9$]Y$^-$;

m is an integer from 1 to 3; n is 0 or an integer from 1 to 4, the sum of m+n being from 1 to 5;

$R_4$, $R_5$ and $R_6$ are, independently from each other, selected from the group consisting of alkyl groups from $C_1$ to $C_{12}$ and phenyl groups; $R_7$ and $R_8$, taken separately, are each selected from the group consisting of hydrogen, alkyl groups from $C_1$ to $C_{12}$ and phenyl groups, or, taken together, represent a group selected from the group consisting of tetramethylene, pentamethylene and 3-oxa-1,5-pentylene; and $R_9$ is hydrogen or an alkyl group from $C_1$ to $C_4$;

M is hydrogen or an alkali metal; and Y is the anion of a monobasic acid;

or

B. Z is nitrogen, $R_1$ is selected from the group consisting of alkyl groups from $C_1$ to $C_8$ and phenyl groups, optionally substituted by 1 to 3 substitutents selected from the group consisting of alkyl and alkoxy groups from $C_1$ to $C_4$, $R_2$ and $R_3$ are, independently from each other, selected from the group consisting of alkyl groups from $C_1$ to $C_{12}$, cycloalkyl groups from $C_5$ to $C_{12}$ and phenyl groups optionally substituted by 1 to 3 alkyl groups from $C_1$ to $C_4$; or $R_2$ and $R_3$ are taken together with the nitrogen to form a 5 to 12-membered ring, optionally comprising further nitrogen or oxygen atoms; and $R_{10}$ and $R_{11}$ are each a phenyl group; or said ligand is represented by the general formula

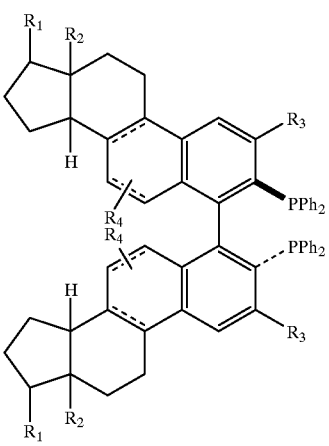

(X)

Ph = phenyl in which $R_1$ is selected from the group consisting of hydrogen, fluoride, alkyl groups, acyl groups, and a group of formula $XR_5$ in which X is oxygen or sulfur and $R_5$ is selected from the group consisting of hydrogen, alkyl groups and aryl groups;

$R_2$ is selected from the group consisting of hydrogen and alkyl groups, with the stereochemistry of the C-$_{13}$, C-$_{14}$ and C-$_{17}$ being α or β;

$R_3$ is selected from the group consisting of hydrogen, fluoride, alkyl groups, aryl groups, trialkylsilyl groups and a group of formula $XR_6$ in which X has the sense indicated above and $R_6$ is selected from the group consisting of hydrogen, alkyl groups, aryl groups and trifluoromethylsulfonyl groups;

$R_4$ is a substituent in position 6 or 7 of the steroide and is selected from the group consisting of hydrogen, fluoride, alkyl groups, aryl groups and a group of formula $YR_7$ in which Y is oxygen, sulfur or a trialkylsilyl group and $R_7$ is selected from the group consisting of hydrogen, alkyl groups, aryl groups and a trifluoromethylsulfonyl group; the B cycle of the steroide being saturated or carrying two double bonds.

2. Process according to claim 1, wherein there is used a ligand of the general formula

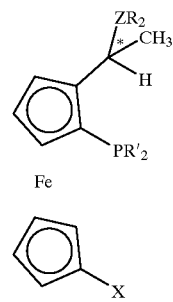

(VIII)

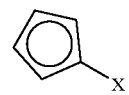

in which the carbon atom marked by the asterisk is an asymmetric carbon atom, X is hydrogen or a bridging group bonded to a polymer as defined in claim 1, Z is a phosphorous atom, and R and R' are, independently from each other, selected from the group consisting of linear and branched alkyl groups from $C_1$ to $C_4$, a cyclohexyl group and phenyl groups which are optionally substituted by 1 to 3 alkyl groups from $C_1$ to $C_4$, which alkyl groups may be partially or entirely fluorinated;

or wherein Z is a nitrogen atom and R and R' are independently from each other selected from the group consisting of linear and branched alkyl groups from $C_1$ to $C_4$, a cyclohexyl group, and phenyl groups which are optionally substituted by 1 to 3 alkyl groups from $C_1$ to $C_4$.

3. Process according to claim 2, wherein there is used a ligand of formula (VIII) in which Z=P and R=tert-butyl, R'=phenyl; or R=R'=cyclohexyl; or R≠R'=cyclohexyl, phenyl; or R=tert-butyl, R'=p-CF$_3$-phenyl; or R=cyclohexyl, R'=p-CF$_3$-phenyl; or R=cyclohexyl, R'=p-tolyl; or Z=N and R=methyl and R'=phenyl.

4. Process according to claim 2, wherein X is a hydrogen atom.

5. Process according to claim 2, wherein X is a group of formula (A)$_n$—B—P in which a) n=0 and B is a group of formula

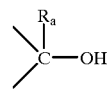

in which $R_a$ is a hydrogen atom or an alkyl group from $C_1$ to $C_{12}$; or b) n=1 and A is a group of formula —[Si(R$_{14}$R$_{15}$)]$_m$R$_{16}$—, in which m is 0 or 1, the groups R$_{14}$ and R$_{15}$ can be identical or different and represent independently from each other a substituent selected from the group consiting of alkyl groups from $C_1$ to $C_{12}$, cycloalkyl groups from $C_3$ to $C_7$, benzyl groups and phenyl groups or, taken together, represent an alkylene group from $C_5$ to $C_{12}$, and R$_{16}$ represents a substituent selected from the group consisting of a phenylene group, unsubstituted alkyl groups from $C_1$ to $C_{12}$ and alkyl groups from $C_1$ to $C_{12}$ substituted by at least one atom selected from the group consisting of halides and hydroxy groups, and B is a group of formula N(R$_{17}$)—C(O)—N(H)—(CH$_2$)$_o$—Si(R$_{18}$)$_{3-p}$—(O)$_p$— or of formula —O—C(O)—N(H)(CH$_2$)$_o$—Si(R$_{18}$)$_{3-p}$—(O)$_p$—, in which R$_{17}$ is hydrogen or an alkyl group from C$_1$ to C$_{12}$, o is an integer from 1 to 12, R$_{18}$ is an alkyl group from C$_1$ to C$_4$ or an alkoxy group from C$_1$ to C$_{12}$ and p is an integer from 1 to 3, and P is silica; or c) n=1 and A is a group of formula —[Si(R$_{14}$R$_{15}$)]$_m$R$_{16}$—, in which m is 0 or 1, the groups R$_{14}$ and R$_{15}$ can be identical or different and represent independently from each other a substituent selected from the group consiting of alkyl groups from C$_1$ to C$_{12}$, cycloalkyl groups from C$_3$ to C$_7$, benzyl groups and phenyl groups or, taken together, represent an alkylene group from C$_5$ to C$_{12}$, and R$_{16}$ represents a substituent selected from the group consisting of a phenylene group, unsubstituted alkyl groups from C$_1$ to C$_{12}$ and alkyl groups from C$_1$ to C$_{12}$ substituted by at least one atom selected from the group consisting of halides and hydroxy groups, and B is selected from the group consisting of
  i) the groups of formulae N(R$_{17}$)—C(O)—, N(R$_{17}$)—C(O)—N(H)—R$_{19}$—N(H)—C(O)— and —O—C(O)—N(H)—R$_{19}$—N(H)—C(O)—, in which R$_{17}$ has the sense given above, R$_{19}$ is a bridging group derived from a diisocyanate selected from the group consisting of substituted and unsubstituted alkylene groups from C$_2$ to C$_{20}$, and substituted and unsubstituted phenylene, naphthylene and biphenylene groups,
  ii) groups capable of reacting with the monomers forming the polymer P by polymerization or copolymerization, and
  iii) groups capable of reacting with the polymer P or with functional groups present on said polymer P, and P is an organic polymer selected from the group consisting of non-functionalized and functionalized polyolefines, polyacrylates, polyisoprenes, polybutadienes, polystyrenes, polyphenylenes, polyvinylchloride, polyvinylidene chloride, polyallyl polymers, polyurethanes, polyethers, polyesters and polyamides.

6. Process according to claim 1, wherein there is used a ligand of formula (XI)

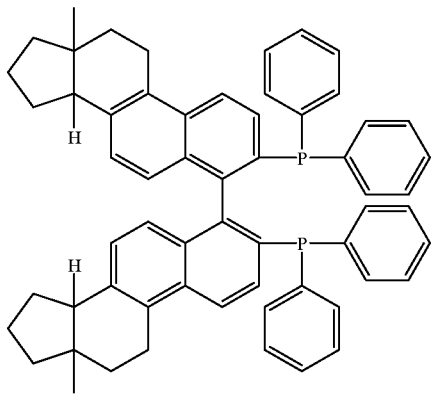

(XI)

or 4,4'-bis(3-diphenylphosphino estra-1,3,5(10),6,8-pentaene.

7. Process according to claim 1, wherein there is used an active Rh complex according to any of the formulae [RhL*(ene)$_2$]$^+$X$^-$, [RhL*(diene)]$^+$X$^-$; [RhL*]$^+$X$^-$ and [RhL*$_2$]$^+$X$^-$, in which L* is a chiral phosphorous ligand as defined in claim 1, "ene" is an olefine selected from the group consisting of ethylene, propylene and butene, "diene" is a diene selected from the group consisting of 1,3-butadiene, 1,3-pentadiene, cyclopentadiene, 1,5-hexadiene, 1,4-cyclohexadiene, 1,4- and 1,5-heptadiene, 1,4- and 1,5-cyclcoheptadiene, 1,4- and 1,5-octadiene, 1,4- and 1,5-cyclooctadiene, and norbornadiene, and X$^-$ is an anion selected from the group consisting of halides, ClO$_4^-$, BF$_4^-$, B(C$_6$H$_5$)$_4^-$, PF$_6^-$, PCl$_6^-$, CH$_3$COO$^-$, CF$_3$COO$^-$, SbF$_6^-$, AsF$_6^-$, CH$_3$SO$_3^-$, FSO$_3^-$, and CF$_3$SO$_3^-$.

8. Process according to claim 7, wherein said diene is selected from the group consisting of norbornadiene and 1,5-cyclooctadiene and said anion X$^-$ is CF$_3$SO$_3^-$.

9. Process according to claim 1, wherein said allyl amine is selected from the group consisting of geranyldiethylamine, neryldiethylamine, cyclohexylgeranylamine, methylcyclohexylgeranylamine and (E)- and (Z)-N,N-diethyl-7-hydroxy-3,7-dimethyl-2-octenylamine.

10. Process according to claim 1, wherein the active complex is used in a concentration of from about 0.05 mole % to about 20 mole % with respect to the substrate.

11. Process according to claim 10, wherein the active complex is used in a concentration of from about 0.1 to about 5 mole % with respect to the substrate.

12. Process according to claim 1, wherein the reaction is carried out at a temperature of from about 0° C. to about 150° C.

13. Process according to claim 12, wherein the reaction is carried out at a temperature of from about 40° to 110° C.

14. Process according to claim 1, wherein the solvent used is tetrahydrofuran.

* * * * *

UNITED STATES PATENT AND TRADEMARK OFFICE
CERTIFICATE OF CORRECTION

PATENT NO. : 6,020,527

DATED : February 1, 2000

INVENTORS : Christian CHAPUIS et al.

It is certified that error appears in the above-identified patent and that said Letters Patent is hereby corrected as shown below:

Column 8, line 38: change "$Cl_4^-$" to --$ClO_4^-$--.

Column 19, Table VIA, Run H: change "$[(NBD)RhCl_2]^- AgSO_2CF_3$" to --$[(NBD)RhCl_2]^- AgSO_3CF_3$--.

Columns 25-26, Example 11, the formula should be corrected to read as follows:

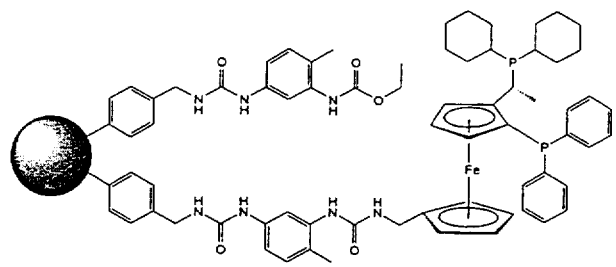

● = polystyrene

UNITED STATES PATENT AND TRADEMARK OFFICE
CERTIFICATE OF CORRECTION

PATENT NO. : 6,020,527
DATED : February 1, 2000
INVENTOR(S) : Christian CHAPUIS et al.

It is certified that error appears in the above-identified patent and that said Letters Patent is hereby corrected as shown below:

Column 28, line 1, the formula should be corrected to read as follows:

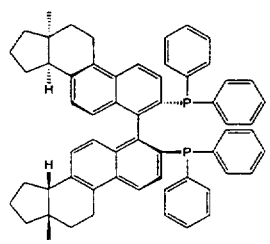

Column 30, line 63: change "-[NR$_7$R$_8$R$_9$]Y$^-$" to -- -[$^+$NR$_7$R$_8$R$_9$]Y$^-$ --.

Signed and Sealed this

Thirteenth Day of February, 2001

Attest:

NICHOLAS P. GODICI

Attesting Officer    Acting Director of the United States Patent and Trademark Office